United States Patent [19]

Benson

[11] Patent Number: 4,823,796

[45] Date of Patent: Apr. 25, 1989

[54] DEFIBRILLATOR CIRCUIT FOR PRODUCING A TRAPEZOIDAL DEFIBRILLATION PULSE

[75] Inventor: Jonathan M. Benson, Oregon City, Oreg.

[73] Assignee: Laerdal Manufacturing Corp., Portland, Oreg.

[21] Appl. No.: 34,487

[22] Filed: Apr. 3, 1987

[51] Int. Cl.⁴ .............................................. A61N 1/36
[52] U.S. Cl. ............................................... 128/419 D
[58] Field of Search .................................... 128/419 D

[56] References Cited

U.S. PATENT DOCUMENTS

| Re. 30,750 | 9/1981 | Diack et al. |
|---|---|---|
| 969,659 | 7/1948 | Valet. |
| 3,093,136 | 6/1963 | Lohr. |
| 3,258,013 | 6/1966 | Druz. |
| 3,263,093 | 7/1966 | Erdmann. |
| 3,275,851 | 9/1966 | Bedingfield. |
| 3,312,837 | 4/1967 | Flynn et al. |
| 3,359,984 | 12/1967 | Daniher et al. |
| 3,389,704 | 6/1968 | Buchowski et al. ........... 128/419 D |
| 3,442,269 | 5/1969 | Druz. |
| 3,481,341 | 12/1969 | Siedband. |

(List continued on next page.)

OTHER PUBLICATIONS

Patent Office Official Gazette Summary of U.S. Pat. No. 3,614,954 of Mirowski, et al.—Electronic Standby Defibrillator.
Patent Office Official Gazette Summary of U.S. Pat. No. 3,614,055 of Mirowski, et al.—Standby Defibrillator and Method of Operation.
Article entitled "Doubling Breakdown Voltage with Cascoded Transistors" by Peter T. Uhler, from *Circuits for Electronics Engineers* (p. 352), Electronics Magazine Book Series (McGraw-Hill Publications Co. 1977).
Silicon Controlled Rectifier Manual (pp. 110–111), Third Edition, General Electric, Rectifier Components Department, Auburn, N.Y.

Semiconductor Power Circuits Handbook (pp. 4–10-/4–13), First Edition, Applications Engineering Department of Motorola Semi-Conductor Products, Inc. (Nov. 1968).
Article entitled "Ventricular Defibrillation by Monophasic Trapezoidal-Shaped Double-Pulses of Low Electrical Enery" by Leon Resnekov, et al., from *Cardiavasc. Res.* (1968) (pp. 261–264).
Article entitled "Electrical Ventricular Defibrillation" by L. A. Geddes for *E. I. Monthly* (1976) (pp. 42–72).
Patent Office Official Gazette Summary of U.S. Pat. No. 3,527,229 of Kempen—"Method and Apparatus for Cardiac Defibrillation".

Primary Examiner—William E. Kamm
Attorney, Agent, or Firm—Klarquist, Sparkman, Campbell, Leigh & Whinston

[57] ABSTRACT

A pulse delivery control signal is applied to and removed from a master or pulse delivery electronic switch to respectively start and terminate the delivery of a trapezoidal waveform defibrillation pulse from charge storage capacitors to a patient. In one specific embodiment, a transfer charge storage circuit is coupled to a capacitor charging circuit for charging as the charge storage capacitors are charged. A transfer switch interconnects the transfer charge storage circuit to a first field-effect transistor switch. In response to a transfer signal, a transfer voltage signal is delivered from the transfer charge storage circuit, through the transfer switch and to the first field-effect transistor. In response, the first field-signal transistor applied the pulse delivery control signal to the master switch. A second field-effect transistor may be included for operating the master switch together with the first field-effect transistor. Voltage detection and energy selection circuits may be employed for detecting when the charge storage capacitors in the circuit are charged to a desired level and for establishing the level to which the capacitors are charged to thereby control the energy delivered by the defibrillation pulses.

24 Claims, 4 Drawing Sheets

U.S. PATENT DOCUMENTS

| | | |
|---|---|---|
| 3,513,850 | 5/1970 | Weber . |
| 3,548,219 | 12/1970 | Lawrie, Jr. et al. . |
| 3,706,313 | 12/1972 | Milani et al. . |
| 3,747,605 | 7/1973 | Cook . |
| 3,772,533 | 11/1973 | Bruckner et al. . |
| 3,782,389 | 1/1976 | Bell . |
| 3,805,795 | 4/1974 | Denniston et al. ............. 128/419 D |
| 3,814,105 | 6/1974 | Howard et al. . |
| 3,860,009 | 1/1975 | Bell et al. . |
| 3,862,636 | 1/1975 | Bell et al. . |
| 3,865,101 | 2/1975 | Saper et al. . |
| 3,886,950 | 6/1975 | Ukkestad et al. . |
| 3,913,588 | 10/1975 | Klomp . |
| 3,952,750 | 4/1976 | Mirowski et al. ............. 128/419 D |
| 3,983,476 | 9/1976 | Konopasek . |
| 4,077,413 | 3/1978 | Partridge . |
| 4,094,310 | 6/1978 | McEachern et al. . |
| 4,096,856 | 6/1978 | Smith et al. . |
| 4,165,749 | 8/1979 | Cansell ........................... 128/419 D |
| 4,233,659 | 11/1980 | Pirkle . |
| 4,316,472 | 2/1982 | Mirowski et al. . |
| 4,323,075 | 4/1982 | Langer . |
| 4,328,808 | 5/1982 | Charbonnier et al. . |
| 4,360,026 | 11/1982 | Venin et al. . |
| 4,372,324 | 2/1983 | Rockwell . |
| 4,432,375 | 2/1984 | Angel et al. . |
| 4,440,172 | 4/1984 | Langer . |
| 4,494,544 | 1/1985 | Lambert . |
| 4,499,907 | 2/1985 | Kallok et al. . |
| 4,504,773 | 3/1985 | Suzuki et al. . |
| 4,506,677 | 3/1985 | Lambert . |
| 4,510,935 | 4/1985 | Spencer . |
| 4,548,203 | 10/1985 | Tacker, Jr. et al. . |
| 4,566,457 | 1/1986 | Stemple . |
| 4,576,170 | 3/1986 | Bradley et al. . |
| 4,578,597 | 3/1986 | Soneda et al. . |
| 4,614,192 | 9/1986 | Imran et al. . |

DEFIBRILLATOR CIRCUIT FOR PRODUCING A TRAPEZOIDAL DEFIBRILLATION PULSE

BACKGROUND OF THE INVENTION

The present invention relates to defibrillator circuits for generating trapezoidal waveform therapeutic electrical pulses. More specifically, the present invention relates to such a defibrillator circuit which is particularly useful in portable defibrillator devices used under emergency circumstances to apply external defibrillation pulses to heart attach victims suffering from ventricular fibrillation.

Two basic defibrillation pulse waveforms are the damped sinusoidal waveform and the trapezoidal waveform. To deliver equal amounts of therapeutic energy to a patient, the maximum voltage required for effective defibrillation using a trapezoidal defibrillation waveform is typically much less than the maximum voltage required when a damped sinusoidal defibrillation waveform is used. Consequently, a trapezoidal waveform defibrillator circuit has a number of advantages over a damped sinusoidal defibrillator circuit. In the first plate, in comparison to damped sinusoidal waveform defibrillators, lower voltages applied to circuit components of trapezoidal waveform defibrillators reduce the stress on parts subjected to these voltages and thereby reduces the likelihood of component failure. Also, because of these lower voltages, smaller, less costly and more commonly available components may be used in a defibrillator circuit employing this trapezoidal waveform technique. In addition, due to the lower voltages involved, it is easier to electrically isolate high voltage sections of a trapezoidal defibrillator circuit for operator safety. Moreover, trapezoidal waveform defibrillator circuits cah have lower internal impedances than damped sinusoidal defibrillator circuits. Therefore, energy is used more efficiently because a smaller proportion of the energy intended to be applied to a patient is dissipated internally by components of the defibrillator circuit.

One prior art electro-mechanical circuit for a trapezoidal waveform ventricular defibrillator is shown in U.S. Pat. No. 3,359,984 of Daniher et al. In this device, a spring biased armature is cocked to a first position. During defibrillation, the armature is released and slides into engagement with a first set of contacts. This couples a first charged capacitor through these contacts to a patient and commences the application of a trapezoidal waveform defibrillation pulse. As the armature continues to slide, the circuit through the first set of contacts is broken and a second set of contacts is engaged. When this occurs, a second charged capacitor is coupled through the second set of contacts to the patient and another defibrillation pulse is applied. This latter pulse continues until such time as the armature slides out of engagement with the second set of contacts. It is difficult to control the amount of energy applied to a patient by such an apparatus. In addition, the repeated making and breaking of high voltage contacts can result in arcing which wears the armature and contacts of such a device.

Another prior art defibrillator of interest is disclosed in U.S. Pat. No. 3,886,950 of Ukkestead et al. In Ukkestead, a plurality of capacitors are connected for charging in parallel and discharging in series upon commencement of a defibrillation discharge cycle. At the start of a defibrillation cycle, the charge from the capacitors is applied to a patient. When the desired energy has been delivered, a silicon controlled rectifier (SCR) based truncate circuit shunts the capacitors to discharge all capacitors that have not previously been discharged during the delivery of a defibrillation pulse.

In addition, U.S. Pat. No. 3,706,313 of Milani et al. discloses a defibrillation circuit in which a charged capacitor, at the start of the defibrillation pulse, is discharged through a patient and a first SCR. To terminate the defibrillation pulse, a second SCR is turned on to short circuit the first SCR and discharge any remaining charge on the capacitors through a path which does not include the patient.

With this approach, as well as with the Ukkestead approach, residual energy in the capacitors, which is typically twenty-five percent of the originally stored energy, is wasted. In many cases, it is desirable to apply more than one defibrillation pulse to a patient. To administer subsequent defibrillation pulses using the Milani and Ukkestead devices, it is necessary to recharge the capacitors of these devices from a totally discharged state. This requires additional time and current from batteries included in a portable defibrillator. This latter drawback can limit the number of defibrillation pulses available from the device before the batteries need recharging.

The background of the invention portion of the Milani disclosure mentions the possibility of turning off a first SCR after a portion of the charge on a capacitor has been discharged to stop a defibrillation pulse. Milani also recites that a substantially trapezoidal waveform defibrillation pulse may be produced in this manner. However, Milani states that such an approach is unreliable because the turn-off mechanisms of SCR devices are less reliable than the turn-on mechanisms. Milani thus teaches away from trying to turn off an SCR to terminate a defibrillation pulse.

Therefore, a need exists for an improved defibrillator circuit for applying trapezoidal waveform defibrillation pulses to a patient.

SUMMARY OF THE INVENTION

The present invention overcomes the aforementioned drawbacks and limitations of prior art devices by providing a novel defibrillation circuit for generating trapezoidal waveform defibrillation pulses.

In accordance with the present invention, a pulse delivery control signal is applied to and removed from a first or master electronic pulse delivery switch to respectively commence and terminate the delivery of a defibrillation pulse to a patient. This pulse delivery switch is in a series path which includes charge storage capacitors, charged by a capacitor charging circuit, and the patient. The pulse delivery control signal may be obtained directly from a transfer signal source. However, in several preferred embodiments, a control circuit is provided with at least one transfer switch for applying the pulse delivery control signal to the pulse delivery switch in response to a transfer signal.

In one specific form of the invention, a first transfer switch comprises a field-effect transistor circuit responsive to the transfer signal to cause the application of the pulse delivery control signal to the pulse delivery switch. This specific form of the invention also includes a second field-effect transistor circuit, the first and second field-effect transistor circuits being operable to apply the pulse delivery control signal to the pulse delivery switch in response to the transfer signal.

As another feature of one illustrated embodiment of the invention, a transfer charge storage circuit is included. This transfer charge storage circuit may be coupled to the capacitor charging circuit for charging as the charge storage capacitors are charged. A second transfer switch interconnects the transfer charge storage circuit with the first transfer switch. In response to the transfer signal, a transfer voltage signal is selectively delivered from the transfer charge storage circuit through the second transfer switch and to the first transfer switch. In response, a defibrillation pulse is delivered to the patient.

As a more specific aspect of the present invention, novel voltage detection circuit may be employed for determining when the charge storage capacitors of the device are charged to a desired level for delivery of a defibrillation pulse of an appropriate energy to the patient.

As a further aspect of the present invention, unique energy selection circuitry may be used for selecting the amount of energy applied to the patient by the defibrillation pulses.

In addition, in combination with other features of the present invention, an abort circuit may be included in the defibrillator for discharging the charge storage capacitors in the event treatment of the patient is not required.

As a still further aspect of the present invention, a second pulse delivery switch mechanism may be included in the series circuit with the charge storage capacitors and patient for selectively coupling and removing the patient from this path. This second pulse delivery switch is typically closed prior to the time a pulse delivery control signal is delivered to the first or master pulse delivery switch and opened following the application of the pulse delivery control signal. As a result, this second switch mechanism is not closing to start the defibrillation pulse or an opening to interrupt the pulse because this is accomplished by the master switch. Therefore, the second switch mechanism is not subject to damage from arcing electrical currents.

As still another aspect of the present invention, exemplary master pulse delivery switch means include a Darlington pair of transistors, a cascode switch, or a bipolar transistor.

It is one object of the present invention to provide an improved defibrillator circuit for applying trapezoidal waveform defibrillation pulses to a patient.

Still another object of the present invention is to provide a defibrillator circuit for producing a trapezoidal waveform defibrillation pulse which is versatile and applicable over a wide range of applications, including those in which defibrillation pulses of varying energy levels are required.

Still another object of the present invention is to provide a defibrillator circuit for producing trapezoidal waveform defibrillation pulses which is extremely safe and easy to use.

A further object of the present invention is to provide a defibrillator circuit for producing trapezoidal waveform defibrillation pulses which minimizes the energy required during use and, in the case of portable units relying on battery power, prolongs the life of the batteries.

These and other objects, features, and advantages of the present invention will become apparent with reference to the following description and drawings.

DETAILED DESCRIPTION OF PREFERRED EMBODIMENTS

Figure 1:
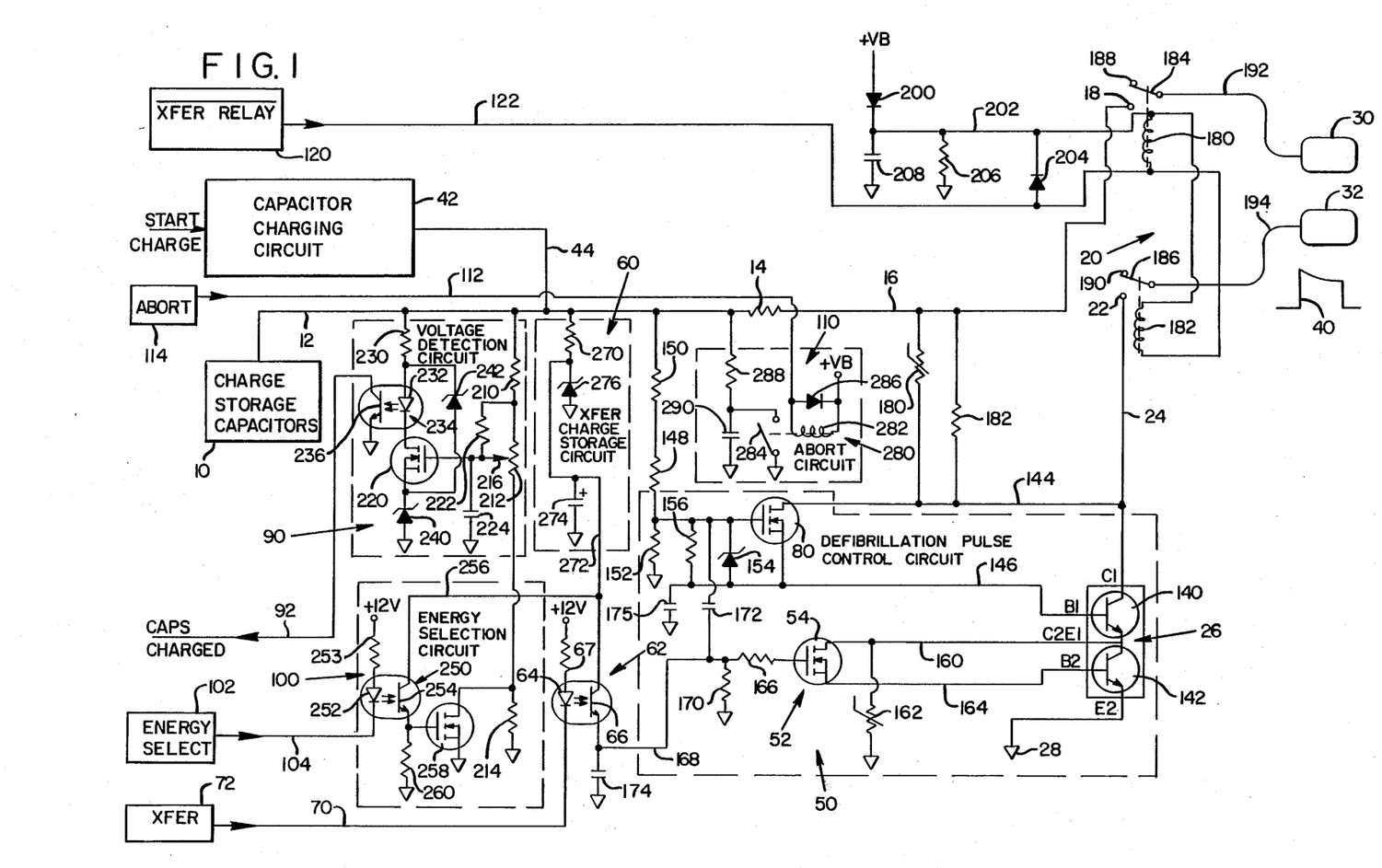
FIG. 1 is an electrical schematic diagram of one form of a defibrillator circuit for producing a trapezoidal waveform defibrillation pulse in accordance with the present invention.

With reference to FIG. 1, this form of defibrillator circuit includes a bank of charge storage capacitors 10 connected by a line 12 through a current limiting resistor 14 and a line 16 to an input terminal 18 of a pulse delivery switch 20. An output terminal 22 of switch 20 is connected by a line 24 to a master pulse delivery switch mechanism 26, which in turn is coupled to ground potential at 28. As explained in greater detail below, pulse delivery switch 20 may comprise a relay controlled switch operable to selectively couple a pair of a patient electrodes 30, 32 to the respective contacts 18 and 22. Electrodes 30, 32 are conventional and are typically positioned on the chest region of a patient. At appropriate times, a trapezoidal waveform shaped defibrillation pulse 40 is delivered between the electrodes and through the patient. Thus, charge storage capacitors 10, the switch 20, electrodes 30, 32 and the master pulse delivery switch 26 are included in a series circuit which also includes the patient (not shown).

A capacitor charging circuit 42, in response to a start charge signal which may either be manually or automatically generated, delivers a charging current on lines 44 and 12 to the charge storage capacitors 10. Capacitor charging circuits are well known in the art. For example, capacitor charging circuits of the type shown in FIG. 13 of U.S. Pat. No. Re 30,750 of Diack et al. or used in a portable Heart*Aid ®R model 97 defibrillator available from Cardiac Resuscitator Corporation of Portland, Oreg. may be used. The capacitor charging circuit 42 may also be electrically isolated from the high voltage portions of the defibrillator circuit in a conventional manner.

When charge storage capacitors 10, which may comprise a bank of capacitors of 500 microfarads of capacitance, is charged to a desired voltage magnitude by the capacitor charging circuit, switch 20 is operated to couple electrodes 30, 32 to the defibrillator circuit. In addition, a pulse delivery control signal, described below, is applied to master pulse delivery switch 26 to drive this switch to a conducting state. When this happens, charge storage capacitors 10 are discharged through the patient until such time as the pulse delivery control signal is terminated and master switch 26 shifts to a nonconducting state. Charge storage capacitors 10 are typically only partially discharged during a defibrillation pulse application cycle. Therefore, capacitor charging circuit 42 is not required to recharge the charge storage capacitors 10 from a totally discharged state for subsequent defibrillation pulses. As a result, less energy is required to charge the charge storage capacitors 10 for the next defibrillation pulse and recharging can be accomplished more rapidly.

The FIG. 1 circuit includes a defibrillation pulse control circuit 50 for controlling the application of the pulse delivery control signal to master pulse delivery switch 26 and thereby for controlling the application of a defibrillation pulse to the patient. The illustrated circuit 50 includes a first transfer switch circuit 52 responsive to a transfer signal for causing the application of the pulse delivery control signal to master switch 26. Switch circuit 52 may comprise a first field-effect transistor 54.

A transfer charge storage circuit 60 is included for providing a transfer voltage signal to field-effect transistor 54. The circuit 60 may be coupled to line 12 for charging by the capacitor charging circuit 42 as charge storage capacitors 10 are charged. A second transfer switch 62 selectively couples the transfer charge storage circuit 60 to the first transfer switch 52. The transfer switch 62 may comprise a conventional optoisolator with a photo diode portion 64 and photo responsive transistor portion 66. The anode of diode portion 64 is coupled through a resistor 67 to a positive voltage source while the cathode of this diode portion is connected by a line 70 to a transfer signal source 72. At times when a defibrillation pulse is to be applied to a patient, a low logic level transfer signal from source 72 is applied to line 70. When this happens, optoisolator 62 conducts and a transfer voltage signal from transfer charge storage circuit 60 is applied to the gate of field-effect transistor 54. This causes the application of a pulse delivery control switch to the master switch 26 and thereby results in the application of a defibrillation pulse to the patient. Transfer signal source 72 may be manually controlled, or may comprise an automatic transfer signal source such as shown in U.S. Pat. No. 4,432, 375 of Angel et al.

Referring again to control circuit 50, the depicted form of this circuit includes a second field-effect transistor 80 operatively coupled to field-effect transistor 54 and to the switch 26 for driving the switch to a conducting state in response to the transfer signal on line 70. The use of a pair of field-effect transistors 54, 80 in the defibrillation pulse control circuit 50 provides a number of distint advantages. For example, this circuit facilitates the control of the starting and stopping of the delivery of high voltage defibrillation pulses to a patient. In addition, these field-effect transistors are operable to effectively divide the voltage drop across cascode transistors forming the FIG. 1 master switch 26 so that neither of these transistors is subjected to excessive voltage.

The FIG. 1 form of the invention also includes a voltage detection circuit 90 coupled to the line 12 for detecting the magnitude of the voltage on the charge storage capacitors 10. When these capacitors are charged to a voltage which corresponds to a reference or threshold voltage setting of the voltage detection circuit 90, a caps charged signal appears on an output line 92 from the voltage detection circuit. This caps charged signal may provide a visual indication to an operator that the capacitors are charged for application of a defibrillation pulse to a patient. Alternately, the caps charged signal may be automatically used, such as described in U.S. Pat. No. 4,432,375 of Angel et al., in determining that the apparatus is ready to deliver an appropriate defibrillation shock to the patient.

An optional energy selection circuit 100 is also shown in the FIG. 1 form of the invention. Energy selection circuit 100 enables the control of the energy delivered to a patient by a defibrillation pulse. In FIG. 1, the energy selection circuit 100 is coupled to the voltage detection circuit 90 so as to vary the reference or threshold voltage at which the charge storage capacitors are fully charged. Capacitor charging circuit 42 halts charging of the charge storage capacitors 10 upon full charging. Consequently, by adjusting the voltage at which full charge occurs, the maximum voltage available for a defibrillation pulse is correspondingly adjusted and the energy available from this pulse is controlled. That is, by controlling the duration of the transfer signal from source 72 and also controlling the maximum voltage on charge storage capacitors 10, accurate control is achieved of the energy delivered to a patient during a defibrillation pulse. An energy select control circuit 102, which may be manually controlled or automatically controlled as in U.S. Pat. No. 4,432,375 of Angel et al., generates an energy select signal on a line 104. This energy select signal, as described below, adjusts the setting of the energy selection circuit 100 to vary the energy delivered by the defibrillation pulse.

In addition, as a safety feature, the defibrillator circuit of FIG. 1 includes an abort circuit 110. This latter circuit is operable in response to a signal on a line 112 from an abort control circuit 114 to selectively discharge the charge storage capacitors 10 at times defibrillation pulses are no longer required. The details of the abort circuit are explained below. However, abort circuit 114 may either be manually operable or automatically controlled, such as described in U.S. Pat. No. 4,432,375 of Angel, et al.

Finally, the circuit of FIG. 1 includes a transfer relay control circuit 120 for generating control signals on a line 122 for the pulse delivery switch 20. These signals may also be manually or automatically generated as described in the previously mentioned Angel et al. patent.

With this overall description in mind, the FIG. 1 circuit will next be described in greater detail. It should be noted that exemplary values for the various components depicted in the circuit of FIG. 1 may be found in Table 1 at the end of this detailed description.

In the FIG. 1 form of the invention, the electronic pulse delivery switch 26 comprises a pair of cascoded transistors 140, 142. The collector of transistor 140 is connected by a line 144 to the drain of field-effect transistor 80 while the source of this field-effect transistor is connected by a line 146 to the base of transistor 140. In addition, the gate of transistor 80 is connected through a pair of resistors 148, 150 to line 12 and also through a resistor 152 to ground. The resistors 148, 150 and 152 effectively bias the circuit so that when switch 26 is off, the collector to emitter voltage of each transistor 140, 142 is no greater than approximately one-half the value of the charge on the voltage storage capacitors. The gate of source voltage of transistor 80 is limited by a twelve volt zener diode 154 connected as shown. A resistor 156, coupled between the gate and source of transistor 80, provides a path for current flow to the line 146 and to the base of transistor 140.

The drain of field-effect transistor 54 is connected by a line 160 to the emitter of transistor 140 and thus to the collector of transistor 142. Also, the drain of transistor 54 is connected through a six hundred and seventy-five volt varistor 162 to ground to limit the voltage at this point to a level that is below the breakdown voltage of transistor 142 and field-effect transistor 54. Resistor 148 is included to bias the circuit so that the voltage of varistor 162 is not exceeded. The source of transistor 54 is connected by a line 164 to the base of transistor 142 while the emitter of this latter transistor is coupled to ground 28. In addition, the gate of transistor 54 is connected through a resistor 166 to a line 168. Line 168 is connected through transfer switch 62 to the transfer charge storage circuit 60 and is also coupled to ground through a resistor 170. In addition, the gates of the transistors 54, 80 are interconnected by a coupling capacitor 172. Filtering capacitors 174, 175 are also included in the circuit of FIG. 1 for filtering purposes. The operation of the defibrillation pulse control circuit 50 is described below.

An eleven hundred volt varistor 180 and parallel resistor 182 are connected between lines 16 and 144 to protect the defibrillator circuit from high voltage signals that otherwise might damage the circuit if accidentally applied. For example, these signals might come from another defibrillator being used simultaneously on the patient.

The illustrated pulse delivery switch 20 comprises a relay controlled switch having first and second relays 180, 182 for controlling associated contacts 184, 186. When current flows through these relays, the contacts 184, 186 are shifted from the position shown in FIG. 1, in which they are coupled to switch terminals 188, 190, into engagement with the contacts 18 and 22. When shifted in this manner line 16 is connected through contact 184 and a line 192 to the electrode 30. Also, in this case line 24 is connected through contact 186 and a line 194 to electrode 32. This places the electrodes in condition for delivery of a defibrillation pulse to a patient. More specifically, a positive voltage source is coupled through a diode 200 and a line 202 to one side of each of the relays 180, 182. The other side of these relays is connected by line 122 to the transfer relay control 120. A diode 204 has its cathode connected to line 202 and its anode connected to line 122 for limiting the magnitude of transient signals across the relays 180, 182. Whenever a low logic signal is applied by transfer relay signal control 120 to the line 122, current flows from the voltage source and through relays 180 and 182. Again, this shifts contacts 184, 186 into engagement with terminals 18 and 22 so as to couple the electrodes 30, 32 to the defibrillation pulse delivery circuit.

Cardiac monitoring circuitry may be connected to terminals 188, 190 for coupling via electrodes 30, 32 to a patient for monitoring the patient's cardiac activity. This monitoring circuitry is automatically disconnected from the patient by contacts 184, 186 at times when a defibrillation pulse is applied.

The voltage detection circuit 90 includes a voltage divider with a resistor 210, potentiometer 212 and resistor 214 connected in series between line 12 and ground potential. The wiper arm 216 of potentiometer 212 is connected to the gate of a field-effect transistor 220. Also, a resistor 222 is connected from the location between resistor 210 and potentiometer 212 to the gate of transistor 220 while the gate of this transistor is coupled through a filtering capacitor 224 to ground. Line 12 is connected through a resistor 230 to the anode of a diode portion 232 of an optoisolator 234 while the cathode of this diode portion is connected to the drain of transistor 220. The caps charge indicating line 92 is connected to the collector of a transistor portion 236 of the optoisolator. The emitter of transistor portion 236 is grounded. A reference voltage establishing zener diode 240, for example, a nineteen volt zener diode, has its anode grounded and its cathode connected to the source of transistor 220. A zener diode 242, such as a five volt zener diode, has its cathode coupled through diode portion 232 to the drain of transistor 220 and its anode connected to the source of this transistor. Zener diode 242 is included for circuit biasing purposes.

The zener diode 240 in effect establishes a reference or threshold voltage for the voltage detection circuit 90. That is, until such time as the charge storage capacitors 10 are charged to a level at which the gate to source voltage of transistor 220 is sufficient to turn on this transistor, current flow through diode portion 232 is blocked and a caps charged indicating signal is not present on line 92. In contrast, when transistor 220 conducts, current flows through diode portion 232, transistor portion 236 conducts and line 92 drops to a low logic level. This indicates that the capacitors 10 are fully charged.

Wiper arm 216 is adjusted to set the gate to source turn on voltage of transistor 220 at the desired level of charge on capacitors 10 for delivering a defibrillation pulse of the appropriate energy level to the patient. For example, the potentiometer 212 may be adjusted such that the voltage on capacitors 10 when fully charged is approximately 1,370 volts for delivery of a 360 joule pulse to a patient. In comparison, circuits administering a damped sinusoidal defibrillation pulse to a patient require a maximum voltage of approximately 4,500 volts in order to deliver a comparable energy defibrillation pulse to a patient.

The energy selection circuit 100 includes an optoisolator 250 with a diode portion 252 having its anode coupled through a resistor 253 to a positive voltage supply and its cathode connected to the line 104, and thus to the energy select control circuit 102. Optoisolator 250 includes a transistor portion 254 having its collector connected by a line 256 to the output of the transfer charge storage circuit 60 and, as explained below, through the transfer charge storage circuit to the line 12. Therefore, the voltage on line 256 and 272 increases as charge storage capacitors 10 are charged. The emitter of transistor portion 254 is connected to the gate of a field-effect transistor 258 and also through a resistor 260 to ground potential. The source of transistor 258 is grounded while the drain of this transistor is coupled to the voltage divider section of the voltage detection circuit 90 at a location between potentiometer 212 and resistor 214.

Whenever energy select control circuit 102 provides a signal on line 104 which is at a logic high voltage level, optoisolator 250 is off and the transistor 258 is also off. Consequently, resistor 214 is not shorted out of the voltage divider section of the voltage detection circuit 90. In contrast, a low logic level signal from energy select control circuit 102 on line 104 permits current to flow from line 256 through the optoisolator 250. When this happens, the voltage at the gate of transistor 258 rises and this transistor turns on. Transistor 258 then provides a short circuit across the resistor 214 and effectively removes this resistor from the voltage divider circuit. This correspondingly adjusts the target voltage at wiper arm 216 at which transistor 220 turns on and indicates that the capacitors 10 are fully charged. For a 200 joule defibrillation pulse, a target voltage of approximately 1,000 volts may be established. The specific energy selection circuit 100 shown in FIG. 1 thus has two-step energy selection capabilities. By including additional energy selection circuits 100, more energy selection steps may be included in the FIG. 1 apparatus.

The transfer charge storage circuit 60 includes a circuit path from line 12 through a resistor 270 and a line 272 to the optoisolator switch 62. Line 256 of the energy selection circuit is connected to line 272. In addition, a charge storage capacitor 274 is coupled to line 272 and ground potential for storing charge as the charge storage capacitors 10 are charged by the capacitor charging circuit. A fourteen volt zener diode 276, with its cathode connected to line 272 and its anode grounded, limits the maximum voltage on the capacitor 274. This zener diode also limits the maximum voltage applied to optoisolator 62 so that its breakdown voltage is not exceeded.

For safety purposes, as previously explained, the circuit of FIG. 1 includes an abort circuit 110 coupled by line 112 to an abort control circuit 114. The abort circuit 110 includes a relay controlled switch 280 having a relay 282 and relay controlled contact 284. One side of relay 282 is connected to a positive voltage source while the other side of the relay is connected to line 112. A diode 286 is connected in parallel with relay 282 with its cathode connected to the positive source and its anode connected to line 112. When abort control circuit 114 delivers a low logic level signal on line 112, current flows through relay 282 and causes contact 284 to shift to the open position shown in FIG. 1. In contrast, a high logic level signal on line 112 causes contact 284 to close. When contact 284 is closed, a capacitor discharge path is provided from charge storage capacitors 10 through line 12, through a resistor 288 and through contact 284 to ground. Consequently, charge storage capacitors 10 may be discharged as desired; for example, when treatment is discontinued.

Figure 2:
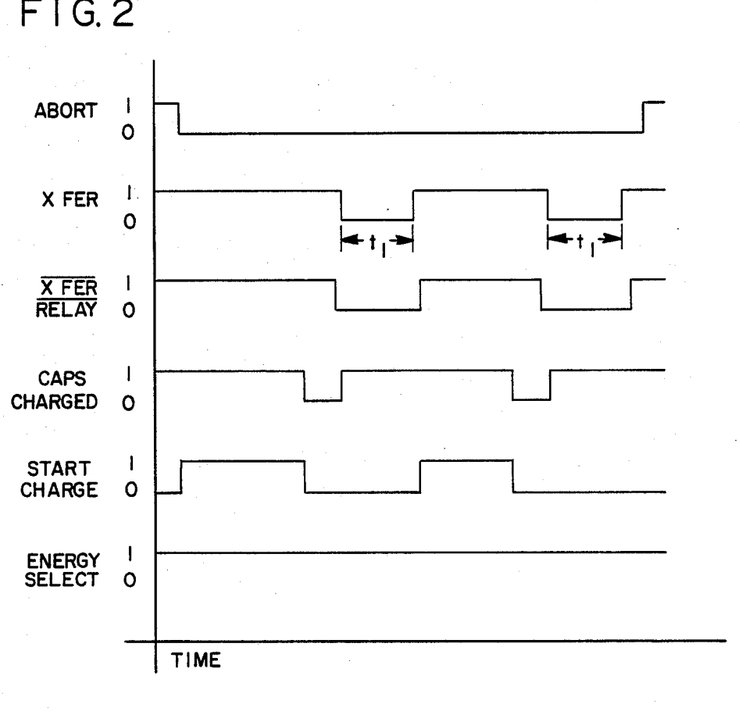
FIG. 2 is a timing diagram illustrating one application of the circuit of FIG. 1.

The operation of the FIG. 1 defibrillator circuit is best understood with reference to FIG. 2. As shown in FIG. 2, the signal from abort control circuit 114 drops to a logic low level at times when the delivery of a defibrillation pulse may be necessary. In response, contact 284 of abort circuit 110 shifts to its open position. In this case, the capacitor discharge path through the abort circuit is blocked.

In the FIG. 2 example, energy select circuit 102 is delivering a logic high signal on line 104 to energy select circuit 100. Consequently, optoisolator 250 and transistor 258 are not conducting. Therefore, resistor 214 is included in the voltage divider network used to establish the voltage at wiper arm 216 of the voltage detection circuit. As mentioned above, the energy select signal is set for delivery of a defibrillation pulse of the appropriate energy level to a patient.

A high logic level start charge signal is then applied to capacitor charging circuit 42 to cause this circuit to begin charging the charge storage capacitors 10 by way of lines 44 and 12. As the capacitors 10 charge, the voltage at wiper arm 216 rises. Simultaneously, the voltage stored by capacitor 274 in the transfer charge storage circuit also rises. When the capacitors 10 are fully charged, the signal on line 92 drops to a logic low level. In addition, the start charge signal drops to a low logic level and charging stops.

Assuming the application of defibrillation pulse is appropriate, the transfer relay signal on line 122 drops from a logic high level to a logic low level. This shifts contacts 184, 186 of switch 20 into engagement with terminals 18, 22 and couples the electrodes 30, 32 to the defibrillation circuit. Preferably, this is accomplished prior to the closing of the master switch 26. Therefore, contacts 184, 186 do not complete a high current circuit path upon closing, which could subject these contacts to damage over time from arcing that would otherwise occur. With this approach, momentarily after contacts 184, 186 are shifted, the transfer signal on line 70 drops to a low logic level for a time t1 as shown in FIG. 2. When this happens, optoisolator switch 62 conducts and a transfer voltage signal from capacitor 274 of the transfer charge storage circuit 60 is applied to the gate of field-effect transistor 54. Field-effect transistors 54, 80 apply a pulse delivery control signal to master pulse delivery switch 26 and causes this switch to conduct. This completes the series path from the charge storage capacitors 10 through electrode 30, the patient, electrode 32 and the master switch to ground. As a result, a trapezoidal waveform defibrillation pulse 40 is applied to the patient. This pulse is terminated at the end of time t1 because, at such time, the transfer signal on line 70 returns to a high logic level. The time t1 is selected to provide an appropriate energy level defibrillation pulse to the patient. When the transfer signal on line 70 is at this high logic level, optoisolator 62 no longer conducts, transistor 54 turns off and master switch 26 no longer conducts.

Assuming a subsequent defibrillation pulse is desired, a start charge signal is again provided to capacitor charging circuit 42 and charging of the capacitors commences. However, because the charge storage capacitors 10 are only partially discharged by the application of the first defibrillation pulse, less time is required to recharge the capacitors to the desired voltage level. This is indicated in FIG. 2 by the fact that the start charge signal is at a high logic level for a shorter period of time than in the previous case where the charge storage capacitors were charged from a fully uncharged state.

Figure 3:
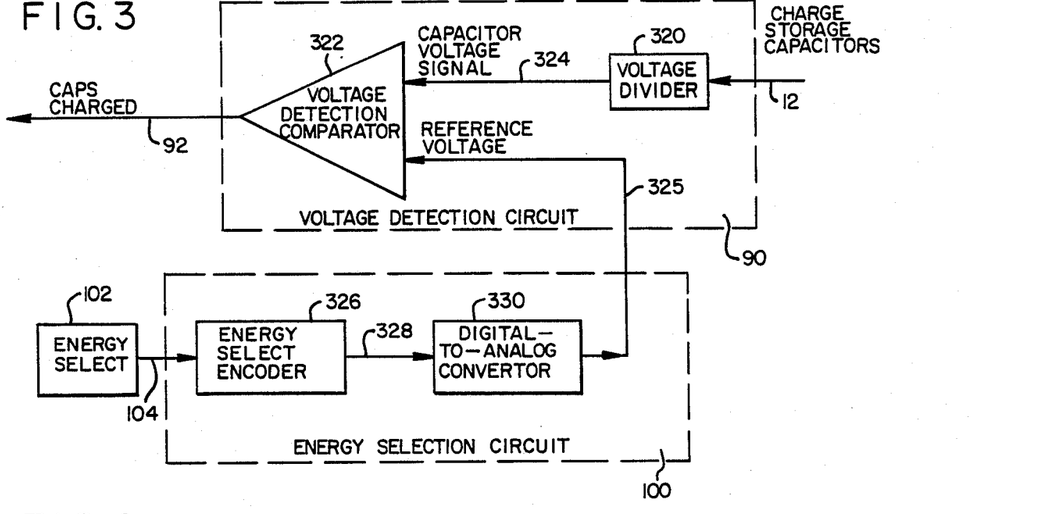
FIG. 3 is a block diagram of alternate forms of voltage detection and energy selection circuits to those shown in FIG. 1.
Figure 4:
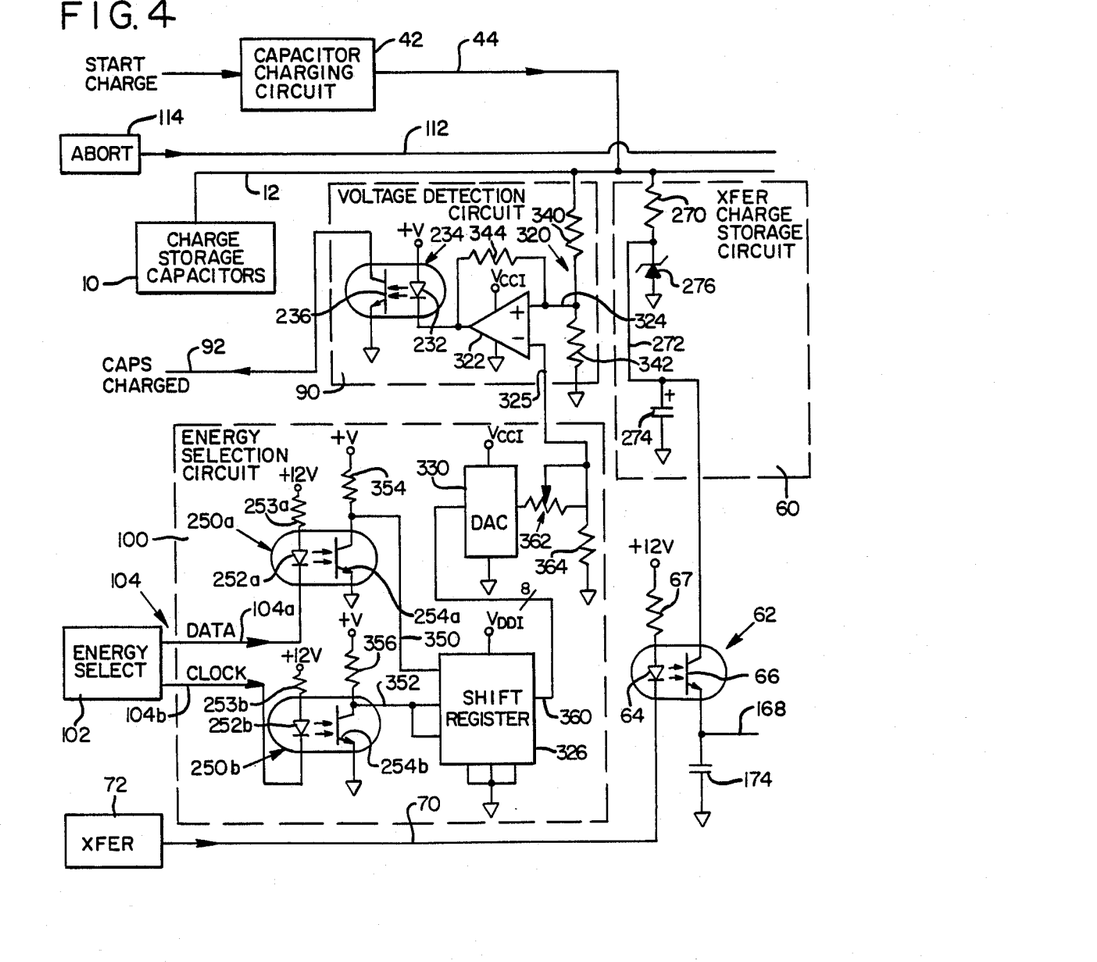
FIG. 4 is a more detailed electrical schematic diagram of the voltage detection and energy selection circuits of FIG. 3.

Alternate forms of voltage detection and energy selection circuits are shown in FIGS. 3 and 4. The FIG. 3 form of voltage detection circuit 90 includes a voltage divider 320 coupled to the charge storage capacitors 10 by line 12 and by another line 324 to a capacitor voltage signal input of a voltage detection comparator 322. The signal applied to this input of the voltage detection comparator constitutes a representation of the magnitude of the instantaneous voltage on the charge storage capacitors 10. Voltage detection comparator 322 has a reference voltage input for receiving a reference voltage signal on a line 325 from the energy selection circuit 100. The output of voltage detection comparator 322 comprises the caps charged indicating signal on line 92 of the device.

The FIG. 3 energy selection circuit 100 includes an energy select encoder 326 for receiving an energy select signal on line 104 from the energy select circuit 102. In the FIG. 3 form of the invention, the energy select signal is a coded digital signal which corresponds to the desired level of energy of defibrillation pulses. The output of the energy select encoder is coupled by a line 328 to a digital-to-analog convertor 330 which converts this signal to a corresponding reference voltage for delivery on a line 325 to the voltage detection comparator.

FIG. 4 illustrates the FIG. 3 voltage detection and energy selection circuits interconnected into the defibrillator of FIG. 1. For convenience, the components of the FIG. 4 circuit which are identical to those of FIG. 1 are assigned an identical number and will not be discussed in detail. As shown in FIG. 4, the voltage divider 320 of the voltage detection circuit includes series connected resistors 340, 342 coupled from line 12 to ground potential. The capacitor voltage signal input line 324 is connected to the point between these two resistors. In addition, voltage comparator 322 may comprise an LM393 differential amplifier with a feedback resistor 344 connected between its output and the input line 324.

The illustrated form of energy selection circuit 100 includes an energy select encoder 326, which may comprise a CD4015 shift register. In this case, energy select control circuit 102 generates data in serial form which corresponds to the desired defibrillation pulse energy level. This data is coupled by a line 104a through an optoisolator 250a to a line 350 which leads to a data input of the shift register 326. A clocking signal from energy select circuit 102 is delivered on a line 104b through a optoisolator 250b and a line 352 to clocking inputs of the shift register 326. The energy select data is fed to circuit 100 in synchronization with clocking signals on line 104b. A positive voltage source is coupled through a resistor 354 to the data input line 350 and also through a resistor 356 to the clock input line 352 of the shift register to provide data and clocking signals of the appropriate magnitude.

Shift register 326 may comprise an eight-bit shift register which produces an eight-bit parallel output at 360 for delivery to the digital-to-analog converter 330. Digital-to-analog converter 330, assuming it is also an eight-bit device, has $2^8$ or 256 different reference voltage outputs. Of course, by altering the size of shift register 326 and the digital-to-analog converter 330, more or fewer reference voltage output signals may be provided. The reference voltage output signal from digital-to-analog converter 330 is fed through a potentiometer 362 and line 325 to the reference voltage input of the voltage detection comparator 322. This input is also coupled through a resistor 364 to ground. The reference voltage output can be adjusted by the potentiometer 362 to compensate for circuit component tolerances.

With the energy selection circuit of FIG. 4, widely varying energy levels of defibrillation or other therapeutic pulses may be selected. For example, lower levels of energy may be selected for pediatric defibrillation while higher energy levels may be designated for other applications.

Figure 5:
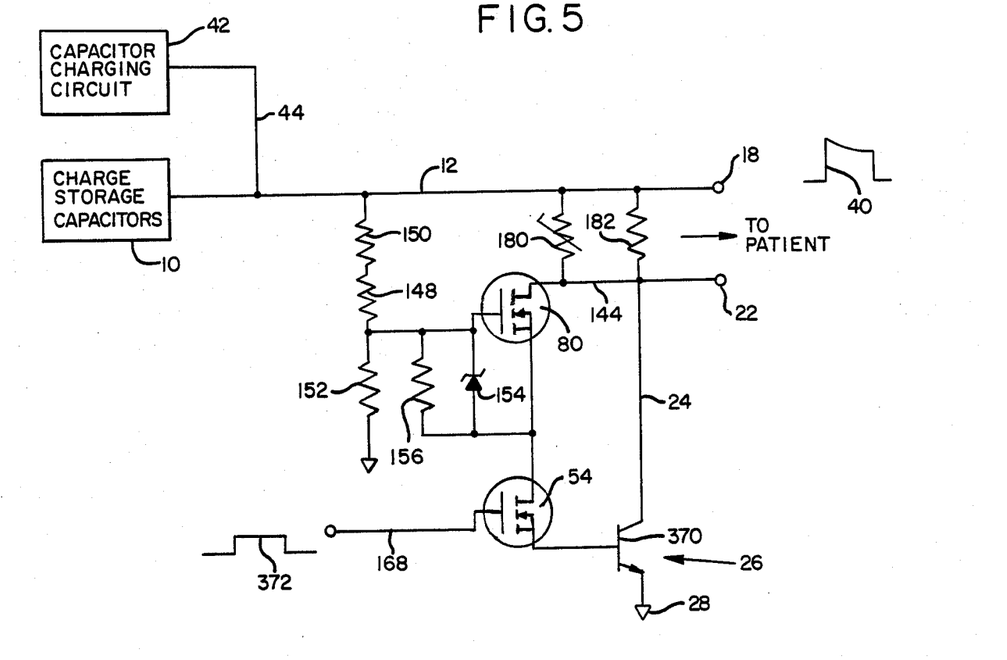
FIG. 5 is an electrical schematic diagram of an alternate form of defibrillator circuit in accordance with the present invention for producing a trapezoidal waveform defibrillation pulse.
Figure 6:
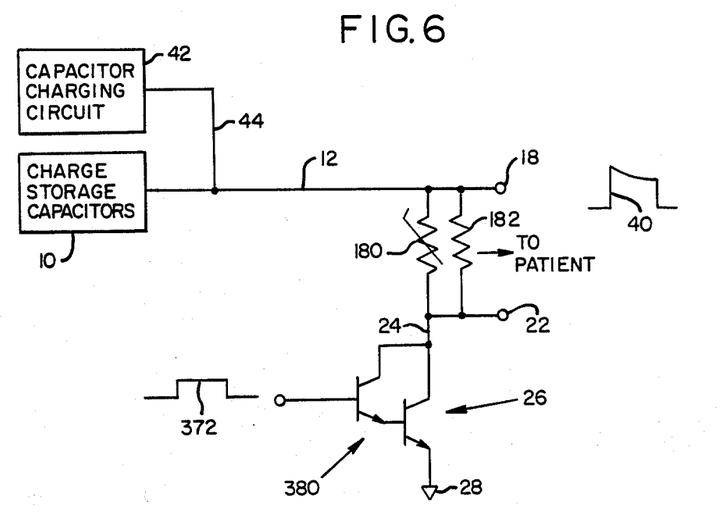
FIG. 6 is an electrical schematic diagram of still another form of a defibrillator circuit in accordance with the present invention for producing a trapezoidal waveform defibrillation pulse.

FIGS. 5 and 6 illustrate alternate versions of defibrillator circuits in accordance with the present invention. Typically, the FIGS. 5 and 6 versions are limited to applications where lower level energy (i.e. 200 joules or less) pulses are required.

In the FIG. 5 form of defibrillator circuit, the energy selection and voltage detection circuits are not shown. In addition, the optional optoisolators have also been eliminated. As shown in FIG. 5, the master switch 26 in this case comprises a bipolar power transistor 370 having its base connected to the source of transistor 54, its emitter grounded, and its collector connected to the line 24 and thus to the patient. Upon the application of a digital pulse 372 to the gate of transistor 354, the pulse 372 being of an appropriate magnitude to turn on transistor 54, transistor 54 conducts. In response, base current is supplied to transistor 370 and it also shifts to a conducting state. In addition, transistor 80 conducts and provides base current to transistor 370 to drive it further into a conducting state. Transistor 80 also reduces the drain to source voltage across transistor 54. When transistor 370 conducts, charge storage capacitors 10 are discharged through the patient and transistor 370 until pulse 372 drops to a low level. When pulse 370 drops, transistor 54 turns off and shuts off the transistor 370. This terminates the defibrillation pulse. It should be noted that the pulse 372 may be obtained directly from the transfer circuit 72. Alternately, a transfer charge storage circuit 60 may be employed as in the FIG. 1 form of the invention.

In the FIG. 6 form of defibrillator circuit, the master switch 26 comprises a Darlington pair of transistors 380. These transistors are driven into a conducting state in response to the transfer signal 372 to administer a defibrillation pulse to a patient. Transistors 380 stop conducting when pulse 372 ends and thereby terminate the defibrillation pulse.

As shown in FIGS. 5 and 6, each of these circuits applies a trapezoidal waveform defibrillation pulse 40 to the patient. The pulse 40 starts when transfer signal 372 shifts to a high voltage level and ends when the transfer signal 372 returns to its initial value.

The table below lists exemplary values for the various components identified in the circuits of FIGS. 1, 4, 5 and 6. It is of course to be understood that the invention is not limited to circuits having components with the following values.

TABLE I

| Reference Number | Component |
| --- | --- |
| 14. | 4 ohm resistor |
| 67. | 2.2 kilohm resistor |
| 148. | 33 kilohm resistor |
| 150. | 200 kilohm resistor |
| 152. | 200 kilohm resistor |
| 156. | 22 kilohm resistor |
| 166. | 1 kilohm resistor |
| 170. | 2.2 kilohm resistor |
| 172. | 180 picofarad capacitor |
| 174. | 0.1 microfarad capacitor |
| 175. | 0.2 microfarad capacitor |
| 182. | 47 kilohm resistor |
| 206. | 100 kilohm resistor |
| 208. | 100 microfarad capacitor |
| 210. | 3 meg ohm resistor |
| 212. | 100 kilohm potentiometer |
| 214. | 16.5 kilohm resistor |
| 222. | 1 meg ohm resistor |
| 224. | 330 picofarad capacitor |
| 230. | 2 meg ohm resistor |
| 253, 253a, 253b | 2.2 kilohm resistor |
| 260. | 1 meg ohm resistor |
| 270. | 3 meg ohm resistor |
| 274. | 22 microfarad capacitor |
| 288. | 1 kilohm resistor |
| 290. | 0.01 microfarad capacitor |
| 340. | 30 meg ohm resistor |
| 342. | 75 kilohm resistor |
| 344. | 7.5 meg ohm resistor |
| 354. | 10 kilohm resistor |
| 356. | 10 kilohm resistor |
| 362. | 5 kilohm potentiometer |
| 364. | 10 kilohm resistor |

Having illustrated and described the principles of my invention with reference to one preferred embodiment, it should be apparent to those persons skilled in the art that such invention may be modified in arrangement and detail without departing from such principles. I claim as my invention all such modifications as come within the true spirit and scope of the following claims.

I claim:

1. A defibrillator circuit for applying trapezoidal defibrillation pulses to a patient comprising:
    means for producing a defibrillation pulse delivery control signal;
    capacitor charge storage means;
    charging circuit means for charging the capacitor charge storage means;
    defibrillation pulse discharge circuit means for coupling the capacitor charge storage means in series with the patient and for selectively delivering a trapezoidal-shaped defibrillation pulse from the capacitor charge storage means to the patient, the discharge circuit means including a first electronic defibrillation pulse delivery switch means in the series path, the first pulse delivery switch means comprising means for shifting to a first conducting state in response to a defibrillation pulse delivery control signal to permit the partial discharge of the capacitor charge storage means through the patient, the first pulse delivery switch means also comprising means for shifting to a second non-conducting state when the pulse delivery control signal is removed to block further discharge of the capacitor charge storage means through the patient, the discharge circuit means including defibrillation pulse delivery control means for selectively delivering the pulse delivery control signal to and removing the pulse delivery control signal from the first pulse delivery switch means to thereby respectively commence and terminate the application of a defibrillation pulse to the patient.

2. A defibrillation circuit according to claim 1 in which the first pulse delivery switch means comprises a Darlington pair of transistor means for shifting to the first conducting state is response to the defibrillation pulse delivery control signal and to the second non-conducting state when the pulse delivery control signal is removed.

3. A defibrillator circuit according to claim 1 in which the defibrillation pulse delivery control means includes means for generating a defibrillation pulse transfer signal and control circuit means responsive to the transfer signal for selectively applying the pulse delivery control signal to and removing the pulse delivery control signal from the first pulse delivery switch means to thereby respectively commence and terminate the application of a defibrillation pulse to the patient.

4. A defibrillator circuit according to claim 3 in which the control circuit means includes first transfer switch means operatively coupled to the first pulse delivery switch means for applying the pulse delivery control signal to the first pulse delivery switch means upon the application of the transfer signal to the first transfer switch means.

5. A defibrillator circuit according to claim 4 in which the first transfer switch means comprises a first field-effect transistor circuit means, the control circuit means also including a second field-effect transistor circuit means coupled to the first pulse delivery switch means and to the first field-effect transistor circuit means for driving the first pulse delivery switch means into a conducting state in response to the transfer signal.

6. A defibrillator circuit according to claim 4 in which the first pulse delivery switch means comprises a cascode switch.

7. A defibrillation circuit according to claim 3 in which the control circuit means includes first transfer switch means operatively coupled to the first pulse delivery switch means for applying the pulse delivery control signal to the first pulse delivery switch means in response to the transfer signal, transfer charge storage circuit means for providing a first transfer switch control signal, second transfer switch means responsive to the transfer signal for selectively coupling the transfer storage circuit means to the first transfer switch means to apply the first transfer switch control signal to the first transfer switch means, the first transfer switch means comprising means for applying the pulse delivery control signal to the first pulse delivery switch means in response to the first transfer switch control signal and thereby in response to the transfer signal.

8. A defibrillator circuit according to claim 7 in which the transfer charge storage circuit means is coupled to the charging circuit means for charging by the charging circuit means as the capacitor charge storage means is charged.

9. A defibrillator circuit according to claim 8 in which the discharge circuit means includes second defibrillation pulse delivery switch means in the series path including the capacitor charge storage means and patient, the second pulse delivery switch means comprising means for closing the series path through the second pulse delivery switch means prior to the application of the pulse delivery control signal to the first pulse delivery switch means and for opening the series path through the second pulse delivery switch means following the application of the pulse delivery control signal to the first pulse delivery switch means.

10. A defibrillator circuit according to claim 1 including energy selection circuit means for selecting the energy to be delivered to a patient by the trapezoidal-shaped defibrillation pulse.

11. A defibrillator circuit according to claim 1 including voltage detection circuit means having means for establishing a reference threshold voltage, the voltage detection circuit means comprising means for comparing the voltage on the capacitor charge storage means to the reference threshold voltage and for indicating that the voltage on such capacitor charge storage means has reached the threshold.

12. A defibrillator circuit according to claim 11 in which the voltage detection circuit means comprises a voltage divider circuit coupled from the charge storage means to ground potential, a detection circuit field-effect transistor having its gate coupled to the voltage divider circuit and its drain coupled to the charge storage means, a zener diode having its cathode coupled to the source of the detection circuit field-effect transistor and its anode coupled to ground potential, and means for detecting and indicating current flow through the detection circuit field-effect transistor and thereby the charging of the charge storage means to the threshold voltage.

13. A defibrillator circuit according to claim 11 including energy selection circuit means for selecting energy to be delivered to a patient by the trapezoidal-shaped defibrillation pulse in response to the pulse delivery control signal, the energy selection circuit means comprising means for selectively varying the reference threshold voltage to thereby select the energy to be delivered to a patient.

14. A defibrillator circuit according to claim 13 in which the energy selection circuit means comprises means for generating a digital signal corresponding to the desired energy, encoder means for receiving the digital signal and for producing an encoder output signal, digital to analog converter means for receiving the encoder output signal and for producing an analog output signal which represents the threshold voltage, whereby variations in the digital signal result in a variation of the threshold voltage and in the energy delivered to a patient by the trapezoidal-shaped defibrillation pulse.

15. A defibrillator circuit for applying trapezoidal defibrillation pulses to a patient comprising:
capacitor charge storage means;
charging circuit means for charging the capacitor charge storage means;
defibrillation pulse discharge circuit means for coupling the capacitor charge storage means in series with the patient and for selectively delivering a trapezoidal-shaped defibrillation pulse from the capacitor charge storage means to the patient;
voltage detection circuit means having means for establishing a reference threshold voltage, the voltage detection circuit means comprising means for comparing the voltage on the capacitor charge storage means to the reference threshold voltage and for indicating that the voltage on such capacitor charge storage means has reached the threshold and thereby that the defibrillator circuit is ready to deliver a defibrillation pulse of a desired energy; and
energy selection circuit means for selecting the energy to be delivered to a patient by the trapezoidal-shaped defibrillation pulse, the energy selection circuit means comprising means for selectively varying the reference threshold voltage to thereby select the energy to be delivered to the patient;
the energy selection circuit means comprising means for generating a digital signal corresponding to the desired energy, encoder means for receiving the digital signal and for producing an encoder output signal, digital to analog converter means for receiving the encoder output signal and for producing an analog output signal which represents the threshold voltage, whereby variations in the digital signal result in a variation of the threshold voltage and in the energy delivered to the patient by the trapezoidal-shaped defibrillation pulse.

16. A defibrillator circuit for applying trapezoidal defibrillation pulses to a patient comprising:
capacitor charge storage means;
charging circuit means for charging the capacitor charge storage means;
defibrillation pulse discharge circuit means for coupling the capacitor charge storage means in series with the patient and for selectively delivering a trapezoidal-shaped defibrillation pulse from the capacitor charge storage means to the patient;
voltage detection circuit means having means for establishing a reference threshold voltage, the voltage detection circuit means comprising means for comparing the voltage on the capacitor charge storage means to the reference threshold voltage and for indicating that the voltage on such capacitor charge storage means has reached the threshold and thereby that the defibrililator circuit is ready to deliver a defibrillation pulse of a desired energy;
energy selection circuit means for selecting the energy to be delivered to a patient by the trapezoidal-shaped defibrillation pulse, the energy selection circuit means comprising means for selectively varying the reference threshold voltage to thereby select the energy to be delivered to the patient; and
the voltage detection circuit means comprising means for establishing a ground potential, a voltage divider circuit coupled from the charge storage means to ground potential, a detection circuit field-effect transistor having its gate coupled to the voltage divider circuit and its drain coupled to the charge storage means, a zener diode having its cathode coupled to the source of the detection circuit field-effect transistor and its anode coupled to ground potential, and means for detecting and indicating current flow through the detection circuit field-effect transistor and thereby the charging of the charge storage means to the threshold voltage.

17. A defibrillator circuit for applying trapezoidal defibrillation pulses to a patient comprising:
capacitor charge storage means;
charging circuit means for charging the capacitor charge storage means;
defibrillation pulse discharge circuit means for coupling the capacitor charge storage means in series with the patient and for selectively delivering a trapezoidal shaped defibrillation pulse from the capacitor charge storage means to the patient, the discharge circuit means including a first electronic defibrillation pulse delivery switch means in the series path, the first pulse delivery switch means comprising means for shifting to a first conducting state in response to a control signal to permit the partial discharge of the capacitor charge storage means through the patient, the first pulse delivery switch means also comprising means for shifting to a second non-conducting state when the pulse delivery control signal is removed to block further discharge of the capacitor charge storage means through the patient;
the discharge circuit means including defibrillation pulse delivery control means for selectively applying the pulse delivery control signal to and removing the pulse delivery control signal from the first pulse delivery switch means to thereby respectively commence and terminate the application of a defibrillation pulse to the patient, the defibrillation pulse delivery control means including first field-effect transistor circuit means coupled to the first pulse delivery switch means for applying the pulse delivery control signal to the first pulse delivery switch means upon the application of a transfer voltage signal to the first field-effect transistor circuit means, transfer charge storage circuit means for providing the transfer voltage signal, transfer switch means for selectively coupling the transfer charge storage means to the first field-effect transistor circuit means to apply the transfer voltage signal to the first field-effect transistor circuit means so as to apply the pulse delivery control signal to the first pulse delivery switch means, the control circuit means also including second field-effect transistor circuit means coupled to the first pulse delivery switch means and to the first field-effect transistor circuit means for applying the pulse delivery control signal to the first pulse delivery switch means to drive the first pulse delivery switch means into a conducting state upon application of the transfer voltage signal to the first field-effect transistor circuit means.

18. A defibrillator circuit according to claim 17 in which the transfer charge storage means is coupled to the charging circuit means for charging by the charging circuit means as the capacitor charge storage means is charged.

19. A defibrillator circuit according to claim 18 in which the discharge circuit means includes second pulse delivery switch means in the series path including the capacitor charge storage means and patient, the second pulse delivery switch means comprising means for closing the series path through the second pulse delivery switch means prior to the application of the pulse delivery control signal to the first pulse delivery switch means and for opening the series path through the second pulse delivery switch means following the application of the pulse delivery control signal to the first pulse delivery switch means.

20. A defibrillator circuit according to claim 19 in which the first pulse delivery switch means comprises a cascode switch.

21. A defibrillator circuit according to claim 18 including voltage detection circuit means for comparing the voltage on the capacitor charge storage means to a reference threshold voltage and for indicating the voltage on such capacitor charged storage means has reached the threshold.

22. A defibrillator circuit according to claim 21 including energy selection circuit means for selecting the energy to be delivered to a patient by the trapezoidal-shaped defibrillation pulse.

23. A defibrillator circuit according to claim 22 including abort circuit means for discharging the capacitor storage means in the event treatment of a patient with defibrillation pulses is unnecessary.

24. A defibrillator circuit according to claim 23 in which the discharge circuit means includes second pulse delivery switch means in the series path including the capacitor charge storage means and patient, the second pulse delivery switch means comprising means for closing the series path through the second pulse delivery switch means prior to the application of the pulse delivery control signal to the first pulse delivery switch means and for opening the series path through the second pulse delivery switch means following the application of the pulse delivery control signal to the first pulse delivery switch means.

* * * * *